United States Patent
Rose et al.

(10) Patent No.: US 7,132,245 B2
(45) Date of Patent: Nov. 7, 2006

(54) ORGAN TRANSPLANT REJECTION AND ASSOCIATED CONDITIONS

(75) Inventors: Marlene Lydia Rose, London (GB); Michael John Dunn, London (GB); Adam Linke, London (GB)

(73) Assignee: Imperial Innovation Limited, London (GB)

( * ) Notice: Subject to any disclaimer, the term of this patent is extended or adjusted under 35 U.S.C. 154(b) by 414 days.

(21) Appl. No.: 10/148,341

(22) PCT Filed: Nov. 29, 2000

(86) PCT No.: PCT/GB00/04553

§ 371 (c)(1),
(2), (4) Date: Nov. 12, 2002

(87) PCT Pub. No.: WO01/40302

PCT Pub. Date: Jun. 7, 2001

(65) Prior Publication Data

US 2005/0277157 A1 Dec. 15, 2005

(30) Foreign Application Priority Data

Nov. 29, 1999 (GB) ................. 9928136.2

(51) Int. Cl.
*G01N 33/53* (2006.01)
(52) U.S. Cl. ................. 435/7.1; 435/7.2; 435/7.91; 435/7.92; 436/512; 436/514
(58) Field of Classification Search ................. 435/7.1, 435/7.2, 7.91, 7.92; 436/512, 514
See application file for complete search history.

(56) References Cited

FOREIGN PATENT DOCUMENTS

| GB | 2 268 935 A | 1/1994 |
|---|---|---|
| WO | WO 02/10755 | 2/2002 |

OTHER PUBLICATIONS

Linke et al. Clin. Experim Immunol. 2001, vol. 126, p. 173-179; Rothe et al. PNAS (1996) vol. 93: 8241-8246.*
Wells et al. Biochemistry 29(37): 8509-8517; "The Protein Folding Problem and Tertiary Structure Prediction, Chapter 14: Computational Complexity Protein Structure Prediction, and the Levinthal Paradox" pp. 492-495.*
Skolnick and Fetrow (2000) Trends in Biotech 18: 34-39; Smith and Zhang (1997) The challenges of genome sequence annotation or 'The devil is in the details'.*
Brenner (Apr. 1999) "Errors in genome annotation." Trends in Genetics 15(4): 132-133;).*
U.S. Appl. No. 10/343,132, filed May 9, 2003, Marlene Lydia Rose et al.
Seshadri, et al., "Identification of a transcript that is down-regulated in senescent human fibroblasts", Journal of Biological Chemistry, 268(25): 18474-18480 (1993).
Kaye, Kenneth M., et al., "Tumor necrosis factor receptor associated factor 2 is a mediator of NF-kappa-B activation by latent infection membrane protein 1, the Epstein-Barr virus transforming protein", PNAS USA, 93(20): 11085-11090 (1996).
Shiba, Kiyotaka, et al., "Human lysyl-tRNA synthetase accepts nucleotide 73 variants and rescues *Escherichia coli* double-defective mutant", Journal of Biological Chemistry, 272(36): 22809-22816 (1997).
Rothe, Mike, et al., "I-TRAF is a novel TRAF-interacting protein that regulates TRAF-mediated signal transduction", PNAS USA 93(16): 8241-8246 (1996).

* cited by examiner

*Primary Examiner*—Long V. Le
*Assistant Examiner*—Jacob Cheu
(74) *Attorney, Agent, or Firm*—Dann, Dorfman, Herrell and Skillman, P.C.

(57) ABSTRACT

The application discloses markers associated with organ transplant rejection and associated conditions, and in particular provides materials and methods for the diagnosis, prognosis or treatment of chronic rejection of transplanted organ such as heart and kidney. Examples of the markers include ribosomal protein L7, β-transducin, 1-TRAF (also known as TANK) or lysyl-tRNA synthetase, or antibodies against these antigens.

16 Claims, No Drawings

ORGAN TRANSPLANT REJECTION AND ASSOCIATED CONDITIONS

FIELD OF THE INVENTION

The present invention relates to organ transplant rejection and associated conditions, and in particular to materials and methods for the diagnosis, prognosis or treatment of chronic rejection conditions such as transplant associated coronary artery disease (TxCAD) or chronic rejection following kidney transplantation.

BACKGROUND OF THE INVENTION

There are generally recognised to be three types of organ rejection: hyperacute, acute and chronic. Hyperacute rejection generally occurs within twenty-four hours of the transplantation, and is readily detected. Acute rejection is generally regarding as rejection occurring within the first six months of transplantation. Acute rejection can be diagnosed relatively easily, for example, in the case of a cardiac transplant by the appearance of certain cell types in biopsy cell infiltrate, and in the case of kidney and liver transplants by the change in the levels of certain serum enzymes. Chronic rejection, generally regarded as that occurring at least six months after transplantation, is very difficult to diagnose clinically, and may not manifest itself clearly for some years, by which time treatment is generally unsuccessful.

In chronic rejection there is typically vasculopathy in the rejected organ. Transplant associated coronary artery disease (TxCAD), a rapidly progressing obliterative vascular disease developing in transplanted heart, is the most important complication after the first year of cardiac transplantation, with an incidence of 40% at five years post transplant. A similar vasculopathy occurs following kidney transplantation where it is designated chronic rejection. Higher incidences of the disease are reported using intravascular ultrasound. Histologically, the grafted vessels become occluded with an intimal lesion consisting of smooth muscle cells, myofibroblasts and deposition of extracellular matrix proteins.

The aetiology of TxCAD remains ill defined and several immunological and non-immunological factors have been reported to associate with the risk of TxCAD. This complicated aetiology means that TxCAD remains difficult to diagnose clinically. The denervated heart, for example, prevents anginal symptoms and the diffuse concentric distribution of the lesions can obscure angiographic evidence of stenosis. Chronic rejection of other organs can also be very difficult to diagnose clinically. For example, in the case of renal transplants, rejection cannot be distinguished from cyclosporin nephrotoxicity.

Immunological damage to transplanted organs continues to be the major complication and significant cause of morbidity and mortality, especially following cardiac transplantation. T cells have been described immunocytochemically beneath the endothelium in atherosclerotic plaques from patients with accelerated coronary artery disease. It is likely, however, that T cells invade the endothelium at an early stage of the disease long before there is angiographic evidence of abnormalities. Integrity of the endothelium is recognised as being a crucial factor in maintaining normal vessel function and endothelial injury is probably the earliest event which initiates all forms or arteriosclerosis. Anti-endothelial antibodies can be highly destructive, for example they cause rapid rejection of xenografted organs. Although there is compelling evidence from experimental models to support a pathogenic role of antibodies in chronic rejections, the association in humans remains far from clear, in particular regarding the specificity of antibodies made after transplantation and whether in fact such antibodies can damage graft tissues.

Until recently, endothelial autoantigens have been characterised using Western blotting. Western blotting methods separate endothelial peptides by one dimensional gel electrophoresis. This method can only display a limited number of antigens because many different peptides, having the same molecular weight but different electrophoretic charges, will appear in the same band. A better approach is to separate endothelial peptides by charge and molecular weight using 2-D electrophoresis and probe the subsequent blots with patient sera.

We have previously used these techniques to identify approximately 40 immunoreative cytosolic proteins of which around 30% could be identified by end terminal amino acid sequencing. The most abundant immunoreactive antigen was identified as being the intermediate filament vimentin, see U.S. Pat. No. 5,716,787 and Wheeler et al, 1995. Accordingly, these references disclose that the cytoskeletal protein vimentin or anti-vimentin antibodies are markers that can be used in the diagnosis of TxCAD or chronic rejection in renal transplantation.

However, 2-D electrophoresis suffers from the problem that it can lack the sensitivity to detect the most immunoreactive proteins as they may not be abundant enough to allow their chemical characterisation. Accordingly, it remains a continuing problem in the art to find markers which can provide an accurate and early diagnosis of chronic rejection.

SUMMARY OF THE INVENTION

Broadly, the present invention relates to markers associated with organ transplant rejection and associated conditions, and in particular provides materials and methods for the diagnosis, prognosis or treatment of chronic rejection, e.g. in conditions such as TxCAD or chronic rejection of kidney transplants. This work arose from the realisation that anti-endothelial antibodies are responsible for endothelial cell activation and damage, which in turn leads to organ transplant rejection.

Without wishing to be bound by any particular theory, the inventors believe that in transplant associated coronary heart disease, humoral autoimmunity or alloimmunity against endothelial cells plays an important role in the pathogenesis of disease. Accordingly, the work leading to the present invention is based on the use of expression cloning to identify the targets recognised by anti-endothelial antibodies in patients with TxCAD. Samples from patients containing antibodies were used to screen a human endothelial cDNA expression library to identify and isolate the corresponding antigens. These antigens were then recovered, subcloned and sequenced and then used in assays.

Accordingly, in a first aspect, the present invention provided the use of the presence or amount of ribosomal protein L7, β-transducin, 1-TRAF (also known as TANK) or lysyl-tRNA synthetase, or antibodies against these antigens, as a marker for the diagnosis and/or prognosis of chronic rejection and associated conditions. In preferred embodiments, the present invention discloses new markers for the serological identification of accelerated coronary artery disease following cardiac transplantation and chronic rejection following kidney transplantation.

In a further aspect, the present invention provides a method of diagnosing chronic rejection or associated conditions, e.g. transplant associated coronary artery disease (TxCAD) or transplanted organ rejection, the method comprising determining the presence or amount of ribosomal protein L7, β-transducin, 1-TRAF or lysyl-tRNA synthetase, or antibodies against these proteins, in a sample from a patient.

In a preferred embodiment, the method comprises the steps of:
  (a) contacting a sample from a patient with a solid support having immobilised thereon a binding agent having binding sites which are capable of specifically binding to the antibody or antigen under conditions in which the antibody or antigen bind to the binding agent; and,
  (b) determining the presence or amount of the antibody or antigen bound to the binding agent.

In one embodiment, step (b) comprises (i) contacting the solid support with a developing agent which is capable of binding to occupied binding sites, unoccupied binding sites or the antibody or antigen, the developing agent comprising a label and (ii) detecting the label to obtain a value representative of the presence or amount of the antibody or antigen in the sample. Examples of labels are set out below. In one convenient embodiment, the label is an enzyme which produce a detectable result by acting on a substrate, e.g. in ELISA type assay. In alternative embodiment, the analyte is detected in step (b) by tagging, to allow it to be detected when it binds to the binding agent in the array. Tagging techniques are well known in the art.

In some embodiments, the method uses immobilised protein in an assay for antibodies (e.g. anti-endothelial antibodies) in a sample which are capable of binding to the protein. Alternatively, the protein may be the target analyte of the assay, e.g. binding to immobilised antibodies on the solid support. Preferred formats of assays are described in more detail below.

In order to provide a method of diagnosis and/or prognosis which is more precise than the prior art, the method can optionally be used to determine the presence or amount of a plurality of protein markers or antibodies associated with organ transplant rejection in a sample from a patient. Conveniently, the assays for the different markers can be carried out employing a plurality of different binding agents, each binding agent being specific for a different analyte in the sample, the binding agents being immobilised at pre-defined (i.e. spatially separated) locations on the solid support.

In a further aspect, the present invention provides a kit for use in the diagnosis or prognosis of chronic rejection by determining the presence or amount of an analyte selected from ribosomal protein L7, β-transducin, 1-TRAF or lysyl-tRNA synthetase, or antibodies against these antigens, in a sample from a patient, the kit comprising:
  (a) a solid support having a binding agent capable of binding to the analyte immobilised thereon;
  (b) a developing agent which is capable of binding to occupied binding sites, unoccupied binding sites or the antibody or antigen, the developing agent comprising a label;
  (c) one or more components selected from the group consisting of washing solutions, diluents and buffers.

In a further aspect, the present invention provides the use of ribosomal protein L7, β-transducin, 1-TRAF or lysyl-tRNA synthetase, or antibodies capable of specifically binding these proteins for the preparation of a medicament for the treatment of chronic rejection and associated conditions and especially transplant associated coronary artery disease (TxCAD) or transplanted organ rejection.

Embodiments of the invention will now be described in more detail by way of example and not limitation.

DETAILED DESCRIPTION

Organ Transplant-Rejection

The present invention concerns the diagnosis, prognosis and treatment of chronic rejection of transplanted organs and associated conditions. As mentioned above chronic rejection, generally regarded as that occurring at least six months after transplantation, is very difficult to diagnose clinically, and may not manifest itself clearly for some years, by which time treatment is generally unsuccessful.

The protein and antibody markers described herein can be used in the diagnosis, prognosis or treatment of rejection of transplanted organs, including transplanted heart, kidney, liver, lung, other solid organs, transplanted tissue comprising endothelial cells such as heart valves, and pathological conditions associated with organ or tissue rejection. In particular, the present invention concerns transplant associated coronary artery disease (TxCAD) and chronic kidney rejection.

In chronic rejection there is typically found to be vasculopathy in the rejected organ. The coronary artery disease known as "accelerated" or "transplant-associated" coronary artery disease is the most serious chronic complication following cardiac transplantation. The abbreviation "CAD" is used herein to denote accelerated or transplant-associated coronary artery disease and does not denote coronary artery disease of any other aetiology. CAD and corresponding vasculopathy in other rejected organs may be regarded either as a manifestation of rejection of a transplanted organ or as a pathological condition associated with rejection. In the present specification CAD and vasculopathy in other organs is treated as a pathological condition associated with rejection but it is to be understood that the description of the condition in those terms is not limiting.

Assays

Methods for determining the concentration of analytes in samples from individuals are well known in the art and readily adapted by the skilled person in the context of the present invention to determine the presence or amount of the protein markers or fragments thereof, or antibodies against the markers in a sample from a patient. The results of such assays can in turn allow a physician to determine whether a patient suffers from a condition or is at risk of developing chronic rejection or an associated condition. It may also allow the physician to optimise the treatment of the conditions. Thus, this allows for planning of appropriate therapeutic and/or prophylactic treatment, permitting streamlining of treatment by targeting those most likely to benefit. The methods are directed to the diagnosis and/or prognosis of organ transplant rejection, in particular transplant associated coronary artery disease (TxCAD) and chronic rejection of kidney transplants.

The methods typically employ a biological sample from patient such as blood, serum, tissue, serum, urine or other suitable body fluids. A preferred patient sample is tissue obtained from endothelial cells from a large vessel or monocytes.

The assay methods for determining the concentration of the protein markers or antibodies typically employ binding agents having binding sites capable of specifically binding to protein markers, or fragments thereof, or antibodies in preference to other molecules. Examples of binding agents include antibodies, receptors and other molecules capable of specifically binding the analyte of interest. Conveniently, the binding agents are immobilised on solid support, e.g. at defined, spatially separated locations, to make them easy to manipulate during the assay.

The sample is generally contacted with the binding agent(s) under appropriate conditions which allow the analyte in the sample to bind to the binding agent(s). The fractional occupancy of the binding sites of the binding agent(s) can then be determined either by directly or indirectly labelling the analyte or by using a developing agent or agents to arrive at an indication of the presence or amount of the analyte in the sample. Typically, the developing agents are directly or indirectly labelled (e.g. with radioactive, fluorescent or enzyme labels, such as horseradish peroxidase) so that they can be detected using techniques well known in the art. Directly labelled developing agents have a label associated with or coupled to the agent. Indirectly labelled developing agents may be capable of binding to a labelled species (e.g. a labelled antibody capable of binding to the developing agent) or may act on a further species to produce a detectable result. Thus, radioactive labels can be detected using a scintillation counter or other radiation counting device, fluorescent labels using a laser and confocal microscope, and enzyme labels by the action of an enzyme label on a substrate, typically to produce a colour change. In further embodiments, the developing agent or analyte is tagged to allow its detection, e.g. linked to a nucleotide sequence which can be amplified in a PCR reaction to detect the analyte. Other labels are known to those skilled in the art are discussed below. The developing agent(s) can be used in a competitive method in which the developing agent competes with the analyte for occupied binding sites of the binding agent, or non-competitive method, in which the labelled developing agent binds analyte bound by the binding agent or to occupied binding sites. Both methods provide an indication of the number of the binding sites occupied by the analyte, and hence the concentration of the analyte in the sample, e.g. by comparison with standards obtained using samples containing known concentrations of the analyte.

In alternative embodiments, the analyte can be tagged before applying it to the support comprising the binding agent.

In a preferred format, the presence or amount of ribosomal protein L7, β-transducin, 1-TRAF (also known as TANK), lysyl-tRNA synthetase, or antibodies against these antigens is determined in an ELISA assay.

There is also an increasing tendency in the diagnostic field towards miniaturisation of such assays, e.g. making use of binding agents (such as antibodies or nucleic acid sequences) immobilised in small, discrete locations (microspots) and/or as arrays on solid supports or on diagnostic chips. These approaches can be particularly valuable as they can provide great sensitivity (particularly through the use of fluorescent labelled reagents), require only very small amounts of biological sample from individuals being tested and allow a variety of separate assays can be carried out simultaneously. This latter advantage can be useful as it provides an assay employing a plurality of analytes to be carried out using a single sample. Examples of techniques enabling this miniaturised technology are provided in WO84/01031, WO88/1058, WO89/01157, WO93/8472, WO95/18376/WO95/18377, WO95/24649 and EP 0 373 203 A. Thus, in a further aspect, the present invention provides a kit comprising a support or diagnostic chip having immobilised thereon a plurality of binding agents capable of specifically binding different protein markers or antibodies, optionally in combination with other reagents (such as labelled developing reagents) needed to carrying out an assay. In this connection, the support may include binding agents specific for analytes such as vimentin, e.g. as disclosed in U.S. Pat. No. 5,716,787.

Expression of Proteins

Following the identification of the protein markers associated with organ transplant rejection, large amounts of the protein may be produced using expression techniques well known in the art. The protein produced in this way may be used as a binding agent, immobilising it on solid support in an assay for antibodies in a sample from a patient, or as an immuogen to produce antibodies. Alternatively, the protein, or fragments thereof, may be used in the therapeutic treatment of organ transplant rejection, i.e. to ameliorate the deleterious effect of the antibodies.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

After transforming the host cells with the nucleic acid encoding the proteins, they an be produced by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers.

Antibodies

In alternative embodiments of the invention, antibodies capable of binding the protein associated with organ transplant rejection may be needed, e.g. for use in assays to determine the presence or amount of a given protein in a sample or for therapeutic use in reducing the deleterious effect of a protein in vivo. Thus, the present invention also provides the production of antibodies having the property of specifically binding to the marker proteins identified herein, or fragments or active portions thereof.

The production of monoclonal antibodies is well established in the art. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2 188 638 A or EP 0 239 400 A. A hybridoma producing a monoclonal antibody may be subject to genetic mutation or other changes, which may or may not alter the binding specificity of antibodies produced.

These antibodies may be specific in the sense of being able to distinguish between the polypeptide it is able to bind and other human polypeptides for which it has no or substantially no binding affinity (e.g. a binding affinity more than $10^3$, more preferably $10^4$ and more preferably $10^5$ times better than to unrelated molecules). Specific antibodies bind an epitope on the molecule which is either not present or is not accessible on other molecules. Antibodies are also useful in purifying the polypeptide or polypeptides to which they bind, e.g. following production by recombinant expression from encoding nucleic acid.

Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al, Nature, 357: 80–82, 1992). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

Antibodies for use in the assays described herein as binding or developing agents may be labelled. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule. One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine. Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. Other techniques that can be sued to label antibodies include tagging, e.g. with a nucleotide sequence which can be amplified by PCR.

The mode of determining binding is not a feature of the present invention and those skilled in the art are able to choose a suitable mode according to their preference and general knowledge.

Antibodies according to the present invention may be used in screening for the presence of a polypeptide, for example in a test sample containing cells or cell lysate as discussed, and may be used in purifying and/or isolating a polypeptide according to the present invention, for instance following production of the polypeptide by expression from encoding nucleic acid therefor. Antibodies may modulate the activity of the polypeptide to which they bind and so, if that polypeptide has a deleterious effect in an individual, may be useful in a therapeutic context (which may include prophylaxis).

An antibody may be provided in a kit, which may include instructions for use of the antibody, e.g. in determining the presence of a particular substance in a test sample. One or more other reagents may be included, such as labelling molecules, buffer solutions, elutants and so on. Reagents may be provided within containers which protect them from the external environment, such as a sealed vial.

Materials and Methods

Patient Samples

We have previously screened approximately 70 patients (transplanted between 1988–1996) who have developed TxCAD for anti-endothelial antibodies (AECA) using Western blotting and the anti-vimentin ELISA. Sequential sera for this group was available at every year after transplantation. In these studies, we used sera from patients at one to eight years post transplant; at this time they had AECA but anti-HLA antibodies (which may be present early after transplantation) were not detectable. Ten 10 sera were selected on the basis of broad reactivity on Western blots (using both whole HUVEC and membrane preparations of HUVEC), ensuring that the samples had high titre IgM AECA using the quantitative ELISA method we have developed (Jurcevic et al, 1998). Previous studies have shown the main AECA subclass made in the TxCAD patients is IgM. As negative controls, sera from 10 healthy volunteers were used.

Endothelial cDNA Library

Positive patient sera identified on both the vimentin ELISA and the Western blot were then immunoscreened on the endothelial cDNA expression library, using a commercially available lambda ZAP endothelial cDNA library (human endothelial 5' stretch, Strategene, Cambridge, UK) which can be screened serologically. The mRNA source of the cDNA library is a pool of 5 individuals' homogenous 1st passage endothelial cells from HUVEC. Cloned colonies were grown under appropriate conditions (selective media containing ampicillin for libraries constructed in pBluescript phagemids) with the addition of IPTG.

Antibody Binding Detection System

Large, 150 mm bacterial plates (containing approximately $10^4$ plaques) were overlaid with IPTG-impregnated nitrocellulose filters for 3.5 hours at 37° C. A bacterial and phage lysate was then used to absorb anti-E. coli antibodies to avoid them contaminating the primary antibody. The binding of patient's antibody to the expressed endothelial proteins on the nitrocellulose filters, after blocking, was identified using an alkaline phosphatase conjugated goat anti-human Ig second antibody. Positive plaques were cut out and the phage eluted was used to re-infect host bacteria. Three rounds of immunoscreening were performed until positive clones are purified to homogeneity. The Uni-ZAP XR vector was used to in vivo excise the phagemid, allowing the insert to be characterised in a plasmid system. Positive clones were then sequenced and matches of DNA sequence for positive clones were determined using the University of Wisconsin GCG Package.

Preparation of Recombinant Proteins of Candidate Antigens for Use as Standards

HIS-tagged recombinant proteins of candidate antigens were prepared by cloning each into a suitable expression vector, typically the T7 expression system (pET) which provides very high levels of protein production using these plasmids. The use of the derivative pET15 is preferred for this work since it adds a short N-terminal affinity tag of 6 histidines to be cloned proteins. These are able to bind to immobilized nickel permitting affinity purification in essentially a single step. Since the interaction between the metal ion and the polyhistidine tail occurs not only in native but also in many denaturing solutions (e.g. urea and guanidine), recombinant proteins that form precipitated inclusion bodies can be readily purified. Typical yields of mammalian proteins expressed from pET plasmids are in the range of 25–200 mg/l culture. After losses in purification, yields of several milligram resulted from small (50–100 ml) bacterial cultures, an amount which is sufficient to establish and perform multiple immunoassays. To tailor the cloned cDNAs for insertion into pET15, PCT was used. The primer for the 3' end of the sequence was derived from the flanking DNA in the pBluescript vector since the isolated clones contain a stop codon encoding the C-terminus. A custom-made primer whose sequence is dictated by the sequences of the protein markers found was made to tailor the 5' end of each of the clones. This primer contained a phased restriction site (NdeI, XhoI or BamHI) to allow in-frame joining of the vector to the cDNA. All clones were checked by DNA sequencing.

Immunoassay Optimisation

Polyclonal antisera against candidate antigens were used as good positive controls for immunoassays. In order to provide proof of principle, the anti-vimentin assay described in Jurcevic et al (1998) was employed, using patients' sera as the positive control. Nevertheless polyclonal antibodies could be useful for assay development and together with monoclonal antibodies could also be used to investigate distribution of antigens in human tissues. Polyclonal and monoclonal antibodies can be made as described above.

ELISA assays can be optimised by using different coating concentrations of the recombinant proteins on different types of plastic, and different coating conditions, times and temperatures. Such optimisation determines whether effects such as pH, ionic strength as charge and hydrophobicity play important roles in the mechanisms by which proteins stick to plastic. Different blocking agents to block vacant protein binding sites on the plastic can also be tried, as can the incubation times for the primary and secondary antibodies. Antibody concentrations 3 SD outside the mean normal antibody concentrations were regarded as significantly elevated. Inter and intra coefficients of variation can calculated to assess the reproducibility of the immunoassays.

Estimating Prevalence and Quantity of Autoantibodies and their Association with Disease After the immunoassays were established using polyclonal sera, a retrospective study of patients' sera was performed. At Harefield we have sequential sera from 70 patients with TxCAD (from 1–8 years after transplantation, 5–8 samples per patient) deep frozen. The secondary (developing) antibody used was alkaline phosphatase-conjugated goat anti-human IgM antisera. Unless positive human standards were found, dilution titration curves of both patient and normal sera was performed in triplicate. Tested immunised rabbit sera was used as the positive control until we find a suitable human positive control containing IgM anti-autoantigen. We will test all the TxCAD sera and normal control sera. Statistical analysis will be performed to assess the significance of antibody levels in patients as compared with controls. The information from these studies was examined in relation to disease activity as assessed by annual angiography (done on all patients) and intra-vascular ultrasound (done on 20% of our patients) by our clinical colleagues at Harefield Hospital.

Expression of Protein Markers

The expression of the protein markers described herein was examined immunocytochemically in microvascular endothelial cells and coronary artery endothelial cells. In addition, we examined whether autoantibodies to such autoantigens alters endothelial cell function. We investigated signal transduction in endothelial cells using ligation by antibodies. Epitope mapping and development of peptide ELISA's was carried out to refine and improve immunoassays.

Results

EXAMPLE 1

Identification of Protein Markers

In a preliminary experiment, sera from ten TxCAD patients was used to screen 40,000 genes from the endothelial cDNA expression library and a total of eight clones were identified, representing candidate autoantigens recognized by anti-endothelial antibodies. Sequencing showed that the antigens were known proteins, available on the GenBank or SwissProt databases under accession codes:

Human ribosomal protein L7: L16558, X52967, X57959 and X57958;

See also Hemmerlich et al (1993), and Seshadri et al (1993).

β-transducin: M24194;

See also Guillemot et al, P.N.A.S. USA, (1989).

1-TRAF, also known as TANK: U59863 and U63830; See also Kaye et al, 1996.

Lysyl-tRNA synthetase: D32053.

The results of this experiment therefore establish the group of endothelial cell autoantigens in TxCAD and may provide new diagnostic markers for organ transplant rejection for the diagnosis or prognosis of conditions such as TxCAD or chronic renal rejection.

EXAMPLE 2

Development of Assays

Ribosomal protein L7 was identified in the screening described above by immunoreactivity to cardiac transplant patient sera at time of CAD diagnosis. His-tagged recombinant protein shows position immunoreactivity by Western blot.

These results were tested using an ELISA screen of 9 patients with TxCAD in the first 3 years of transplantation. This showed a prevalence of $5/9=55.6\%$ as compared to normal control sera (positive cut-off set at mean +2SD of normal range). This is compared to $1/10=10\%$ prevalence in non-CAD transplant patients.

Statistical analysis conducted by Fisher's exact test.

Contingency table:

|  | CAD | non-CAD |
| --- | --- | --- |
| RPL7 −ve | 4 | 9 |
| RPL7 +ve | 5 | 1 |

Significant association at $p<0.05$.

Thus, these results demonstrate that the proteins described herein such as ribosomal protein L7 are good candidate antigens or autoantigens for the diagnosis of transplant rejection in conditions such as TxCAD.

REFERENCES

The references mentioned herein are all expressly incorporated by reference.

U.S. Pat. No. 5,716,787 (Dunn et al).
Wheeler et al, J. Heart Lung Transplant, 14:S188–97, 1995.
Jurcevic et al, Transplantation, 65:1197–1202, 1998.
Hemmerlich et al, Nucleic Acids Res., 21–223–231, 1993.
Seshadri et al, J. Biol. Chem., 268:18474–18480, 1993.
Kaye et al, P.N.A.S. USA, 93:11085–11090, 1996.
Guillemot et al, P.N.A.S. USA, 86(2):4594–4598, 1989.

The invention claimed is:

1. A method for diagnosis or prognosis of chronic rejection of a transplanted organ or transplanted tissue in a patient who has received said transplanted organ or transplanted tissue, the method comprising determining an amount of an antigen which is ribosomal protein L7, or an antibody capable of specifically binding said antigen in a sample from said patient, wherein an increase in amount of said antigen or said antibody in said patient, compared to a normal control, is indicative of said chronic rejection.

2. The method of claim 1, wherein said antigen further comprises vimentin or said antibody further comprises anti-vimentin antibodies.

3. The method of claim 1, comprising determining an increase in amount of a plurality of said antibodies associated with chronic rejection in a single sample, including said anti-vimentin antibodies.

4. The method of claim 1, wherein said transplanted organ is selected from the group consisting of transplanted heart, kidney, liver or lung.

5. The method of claim 1, wherein said transplanted tissue comprises endothelial cells.

6. The method of claim 1, wherein said transplanted tissue is in the form of a heart valve.

7. The method of claim 1, wherein the chronic rejection is transplant associated coronary artery disease (TxCAD) or chronic rejection of a kidney transplant.

8. The method of claim 1, wherein the sample comprise endothelial cells of a large vessel or monocytes.

9. The method of claim 1, wherein the method comprises the steps of:
(a) contacting a sample from a patient with a solid support, having immobilised thereon a binding agent having binding sites which are capable of specifically binding to the antibody or antigen, under conditions in which the antibody or antigen bind to the binding agent; and
(b) determining an increase in amount of the antibody or antigen bound to the binding agent.

10. The method of claim 9, wherein step (b) comprises (i) contacting the solid support with a developing agent which is capable of binding to occupied binding sites, unoccupied binding sites or the antibody or antigen, the developing agent comprising a label (ii) detecting the label to obtain a value representative of an or amount of the antibody or antigen in the sample.

11. The method of claim 10, wherein the label is a radioactive label, a fluorophor, a phosphor, a laser dye, a chromogenic dye, a macromolecular colloidal particle, a latex bead which is coloured, magnetic or paramagnetic, an enzyme which catalyses a reaction producing a detectable result or the label is a tag.

12. The method of claim 9, wherein in step (b) the analyte is labelled to allow its detection when it has bound to the binding agent.

13. The method of claim 9, wherein the binding agent immobilised on the solid support is ribosomal protein L7 or a fragment of ribosomal protein L7.

14. The method of claim 9, wherein the binding agent immobilised on the solid support is an antibody which is capable of binding to ribosomal protein L7.

15. The method of claim 1, comprising determining an increase in amount of a plurality of said antibodies associated with chronic rejection in a single sample.

16. The method of claim 15, wherein the method employs a plurality of binding agents immobilised at predefined locations on the solid support.

* * * * *